United States Patent
Ramu et al.

(10) Patent No.: US 7,579,734 B2
(45) Date of Patent: Aug. 25, 2009

(54) APPARATUS AND METHOD THAT PREVENT FLUX REVERSAL IN THE STATOR BACK MATERIAL OF A TWO-PHASE SRM (TPSRM)

(75) Inventors: Krishnan Ramu, Blacksburg, VA (US); Savio Nimal Lobo, Blacksburg, VA (US)

(73) Assignee: Panaphase Technologies, LLC, Midlothian, VA (US)

( * ) Notice: Subject to any disclaimer, the term of this patent is extended or adjusted under 35 U.S.C. 154(b) by 198 days.

(21) Appl. No.: 10/549,800

(22) PCT Filed: Mar. 17, 2004

(86) PCT No.: PCT/US2004/008114

§ 371 (c)(1), (2), (4) Date: Aug. 14, 2006

(87) PCT Pub. No.: WO2004/084375

PCT Pub. Date: Sep. 30, 2004

(65) Prior Publication Data

US 2006/0273680 A1     Dec. 7, 2006

Related U.S. Application Data

(60) Provisional application No. 60/454,630, filed on Mar. 17, 2003.

(51) Int. Cl.
*H02K 17/42* (2006.01)

(52) U.S. Cl. .................... 310/168; 310/166

(58) Field of Classification Search .............. 310/162, 310/166, 168
See application file for complete search history.

(56) References Cited

U.S. PATENT DOCUMENTS

| | | | |
|---|---|---|---|
| 3,956,678 | A | 5/1976 | Byrne et al. |
| 5,146,127 | A | 9/1992 | Smith |
| 6,051,903 | A | 4/2000 | Pengov |
| 6,194,805 | B1 | 2/2001 | Heese et al. |
| 7,015,615 | B2 * | 3/2006 | Ramu et al. ............. 310/168 |

OTHER PUBLICATIONS

PCT International Search Report dated Mar. 21, 2005.

* cited by examiner

*Primary Examiner*—Dang D Le
(74) *Attorney, Agent, or Firm*—Dickinson Wright, PLLC (57) ABSTRACT

A TPSRM may include a stator, having a plurality of poles and a ferromagnetic or iron back material, and a rotor having a plurality of poles and a ferromagnetic or iron back material. A current flowing through coils wound around a first set of the plurality of stator poles induces a flux flow through the first set of stator poles and portions of the stator back material during a first excitation phase. A current flowing through coils wound around a second set of the plurality of stator poles induces a flux flow through the second set of stator poles and portions of the stator back material during a second excitation phase. The numbers of stator and rotor poles for this TPSRM are selected such that substantially no flux reversal occurs in any part of the stator back material as a result of transitioning between the first and second excitation phases.

20 Claims, 10 Drawing Sheets

APPARATUS AND METHOD THAT PREVENT FLUX REVERSAL IN THE STATOR BACK MATERIAL OF A TWO-PHASE SRM (TPSRM)

CROSS-REFERENCE TO RELATED APPLICATIONS

This application claims priority to U.S. Provisional Application No. 60/454,630 and incorporates by reference this provisional application in its entirety into the present application (see Appendix A).

Additionally, the application hereby incorporates by reference the disclosures provided in Applicant's co-pending PCT International Application Nos. PCT/US03/16627, PCT/US03/16628, PCT/US03/16629, PCT/US03/16630, and PCT/US03/16631.

BACKGROUND OF THE RELATED ART

There is an emerging interest in very high speed machines, having speeds in the range of 20,000 to 60,000 revolutions per minute (rpm), for use in appliances, aerospace, and other applications. The foremost features that are required for these machines are high efficiency and low acoustic noise. For high efficiency operation of these machines, it is important to examine the dominant effects of each and every loss in the machine. There are three dominant losses to be considered in these machines that impose significant design and operational constraints. These dominant losses are: (1) copper or resistive losses, (2) core losses, and (3) frictional and winding losses.

Copper or resistive losses result from the flow of current in the stator windings. The windings invariably have resistances, and currents in them produce a voltage drop, v, equal to the current, i, times the resistance, R, expressed as $v=Ri$. Since a current is flowing through the resistive element, the voltage drop produces a power loss, p, across the windings equal to the current times the voltage drop, which, in turn, equals the resistance times the square of the current, which is expressed as $p=vi=i^2R$. For a given power, if the current is minimized, then the only parameter to impact the resistive power loss is its resistance.

The resistance for a given winding varies with its temperature and a skin effect. Temperature sensitivity is determined by a physical coefficient of the winding material and the temperature rise in the windings due to their excitation. The temperature rise can be controlled by a cooling arrangement, and its upper limit is determined by the thermal capability of the winding's insulator material. Therefore, there is not much that can be done to reduce the resistive losses beyond optimizing the winding material and its cooling arrangement.

The skin effect is due to the frequency of the current that is flowing in the winding and is controlled by the phase switching frequency (PSF), which is different from the pulse width modulation (PWM) frequency. The PSF is determined by how many times a phase experiences current per unit time (i.e., a second) and is determined by the number of poles of the switched reluctance machine (SRM). Therefore, the PSF can be minimized by minimizing the number of poles and operating the machine at lower speed. While the pole numbers can be minimized, the upper speed limit is not determined by the machine but by the application, and, hence, the upper speed (i.e., the highest speed that the machine will experience) is a dominating factor in the machine design.

In the final analysis, it can be deduced that the resistive losses are determined by: (a) temperature sensitivity of the winding material and (b) frequency of the alternating current (ac) component of the current, primarily that of the phase switching frequency. The frequency of the current's ac component is determined by the number of poles of the rotor and stator and by the upper speed of the machine, which is determined by the application and not by anything one can do in the machine design. Therefore, the upper speed of the machine is an independent variable. The temperature sensitivity of the winding material, the frequency of the ac component, and the number of rotor and stator poles can, however, be controlled by the machine designer, within the constraints of the physical characteristics of materials and the necessary pole numbers. Therefore, the resistive losses can be minimized to an extent.

Besides resistive losses, core losses constitute another type of the dominant losses affecting TPSRM design. The core material of a TPSRM experiences a loss due to the varying flux flow in it. The core losses consist of two parts, hysteresis loss and eddy current loss. The hysteresis loss is influenced by the frequency of the flux and flux density in the material and a physical factor of the material. The frequency of the flux is determined by the phase switching frequency, which in turn is determined by the upper speed of the machine. Assuming that flux density is kept at a desired level to generate the required torque, then the factor that is under the control of the designer is the phase switching frequency, but only to an extent as explained above.

Eddy current loss is due to the flow of eddy currents in the laminations and is a function of the square of the frequency and the square of the flux density, as well as other variables, such as the square of the thickness of the lamination material. The thickness of the lamination materials is determined primarily by the cost, and, hence, it is prefixed for each and every application. Therefore, to minimize the eddy current loss, the designer has to minimize the flux density and phase switching frequency.

From the above discussion, it may be seen that is important to reduce the frequency of the phase flux and the magnitude of flux density in the material, to minimize core losses.

The third type of dominant loss affecting TPSRM design is friction and winding loss. This type of loss is a function of the rotor and stator pole shapes and the air gap between them. Given an electromagnetic design of the stator and rotor pole shapes, there is not much that can be done to reduce the friction and winding losses, other than filling the rotor interpolar space with a magnetically inert material, so that the rotor is cylindrical. Also, the stator may be constructed with a thermally-conducting, but magnetically inert, material between the coils of each pole and its adjacent pole, so the stator's inner surface is full of material with no gap other than the air gap in its vicinity. But this is a cost issue, and, therefore, it may not be possible for all applications, particularly for low-cost applications, such as in home appliances.

From the above discussion of the various machine losses, it may be discerned that it is important to minimize all the core loss components, but most importantly the ones that will dominate in the final analysis, related to electromagnetics in very high speed machines. These components can be minimized by controlling the flux density and also by minimizing the frequency of the flux in the materials. Once the pole numbers and upper speed are fixed, the frequency of the flux is also fixed. Thereafter, the design variables available to the designer for minimizing core losses are few or nonexistent. Examining very closely the core losses for various parts of the machine, such as the stator and rotor poles and the stator and rotor back irons, a degree of freedom in tackling the core losses becomes evident. That is, the designer can minimize the core losses in each and every part separately. The core losses for these parts are described below.

The stator and rotor back irons usually have bipolar flux in most SRM machines and experience flux reversals. In the stator poles, the flux density should be maximized for a minimum of material weight. Stator poles do not experience flux reversals. The flux in the rotor poles is also bipolar and designed not to exceed the maximum peak flux density of the materials.

Figure 2:
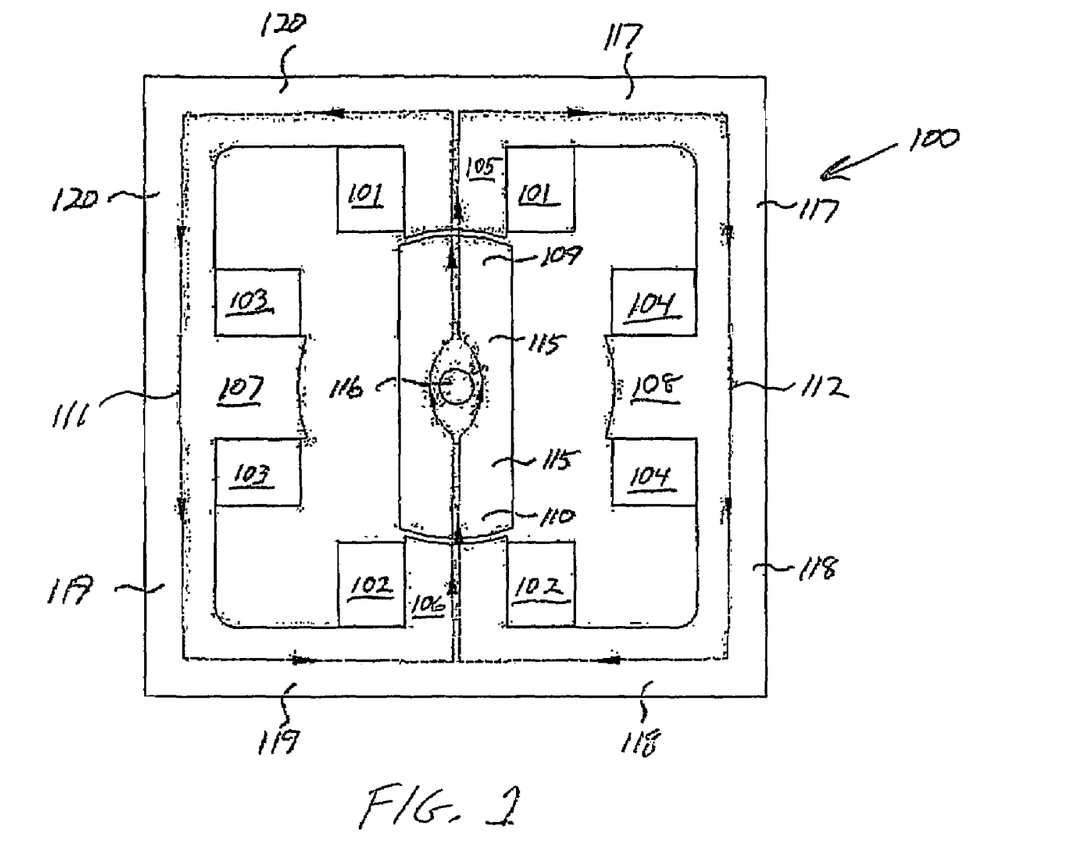
FIG. 2 illustrates the TPSRM of FIG. 1 and its flux paths when phase B is excited.

FIG. 1 illustrates a related art TPSRM having 4 stator poles and 2 rotor poles (a 4/2 stator/rotor pole combination) and the machine's flux paths when phase A is excited. FIG. 2 illustrates the TPSRM of FIG. 1 and its flux paths when phase B is excited. Phase A consists of windings 101 and 102 on diametrically opposite stator poles 105 and 106 connected in series, though they could alternatively be connected in parallel. Likewise, phase B consists of series (or parallel) connected windings 103 and 104 on diametrically opposite stator poles 107 and 108. The flux paths for phase A's stator poles 105 and 106, when excited and aligned with rotor poles 109 and 110, are identified by reference characters 111 and 112. Similarly, the flux paths for phase B's stator poles 107 and 108, when excited and aligned with rotor poles 109 and 110, are identified by reference characters 113 and 114. As may be determined by inspection of FIGS. 1 and 2, stator poles 105-108 do not experience flux reversal for unidirectional current excitation of phases A and B. However, rotor poles 109 and 110 do experience flux reversal as they move from one stator pole (say phase A's) to another stator pole having the same phase. Likewise, rotor back iron 115, which includes the regions between rotor poles 109 and 110 and around shaft 116, also undergoes flux reversal. Similarly, stator back iron segments 117 and 119 experience flux reversal. Stator back iron segment 117 is located in the region between stator poles 105 and 108, stator back iron segment 118 is located in the region between stator poles 106 and 108, stator back iron segment 119 is located between stator poles 106 and 107, and stator back iron segment 120 is located between stator poles 105 and 107.

The above-described flux reversals create: (i) forces in the opposite direction for each flux reversal, thereby causing stator acceleration and, hence, higher acoustic noise generation; and (ii) increased core losses.

SUMMARY OF THE INVENTION

An object of the present invention is to overcome the above-described problems and limitations of the related art.

Another object of the invention is to provide a two-phase switched reluctance machine (TPSRM) that eliminates electromagnetic flux reversals in the ferromagnetic or iron back material of its stator.

Still another object of the invention is to provide a TPSRM that limits the number of electromagnetic flux reversals in the ferromagnetic or iron back material of its rotor to one per revolution of the rotor.

A further object of the invention is to provide a TPSRM that reduces acoustic noise generation at high operating speeds.

A further object of the invention is to provide a TPSRM that reduces core losses.

These and other objects of the invention may be achieved in whole or in part by a TPSRM that includes a stator, having a plurality of poles and a ferromagnetic or iron back material, and a rotor having a plurality of poles and a ferromagnetic or iron back material. A current flowing through coils wound around a first set of the plurality of stator poles induces a flux flow through the first set of stator poles and portions of the stator back material during a first excitation phase. A current flowing through coils wound around a second set of the plurality of stator poles induces a flux flow through the second set of stator poles and portions of the stator back material during a second excitation phase. The numbers of stator and rotor poles are selected such that substantially no flux reversal occurs in any part of the stator back material as a result of transitioning between the first and second excitation phases.

The objects of the invention may also be achieved in whole or in part by a TPSRM that includes a stator, having a plurality of poles and a ferromagnetic or iron back material; and a rotor having a plurality of poles and a ferromagnetic or iron back material. A current flowing through coils wound around a first set of the plurality of stator poles induces a flux flow through the first set of stator poles and portions of the stator back material during a first excitation phase. A current flowing through coils wound around a second set of the plurality of stator poles induces a flux flow through the second set of stator poles and portions of the stator back material during a second excitation phase. The numbers of stator and rotor poles are selected such that a flux induced by each of the first and second excitation phases flows through a path encompassing about two-thirds of the circumference of each of the rotor and stator back materials.

The objects of the invention may be further achieved in whole or in part by a method of operating a TPSRM that includes: (1) inducing an electromagnetic flux to flow through a first set of poles of a stator of the TPSRM during a first excitation phase, (2) inducing an electromagnetic flux to flow through a second set of poles of the stator during a second excitation phase, and (3) transitioning between the first and second excitation phases without creating a substantial flux reversal in a ferromagnetic or iron back material of the stator.

BRIEF DESCRIPTION OF THE DRAWINGS

Preferred embodiments of the present invention will now be further described in the following paragraphs of the specification and may be better understood when read in conjunction with the attached drawings, in which:

FIG. 1 illustrates a related art TPSRM having 4 stator poles and 2 rotor poles and the TPSRM's flux paths when phase A is excited;

DETAILED DESCRIPTION OF THE INVENTION

The present invention endows the machine designer with a degree of freedom for enhancing machine performance by providing an additional variable for reducing core losses. The invention completely eliminates flux reversals in the stator back iron of a two-phase switched reluctance machine (TPSRM) and reduces the number of flux reversals in the rotor back iron, thereby reducing the flux density in these iron parts and controlling both the hysteresis and eddy current losses in them. This leads to minimization of the core losses in the machine and maximization of its operational efficiency. Further, by eliminating the stator flux reversals, the acoustic noise generated by such reversals is minimized.

The invention uniquely provides a two-thirds utilization ratio of the stator to rotor back iron sections serving to convey flux at any given time of the TPSRM's operation, so as to reduce the size of the flux path. TPSRMs having a combination of six stator poles and three rotor poles (i.e., a 6/3 TPSRM) or six stator poles and nine rotor poles (i.e., a 6/9 TPSRM) provide such a two-thirds utilization ratio and its resultant smaller flux path. A smaller flux path requires less magneto motive force (mmf), thereby providing higher efficiency operation. Furthermore, the core losses in the lamination material decrease, since core losses are related to the volume of the material that is covered by the flux path.

Figures 3A, 3B:
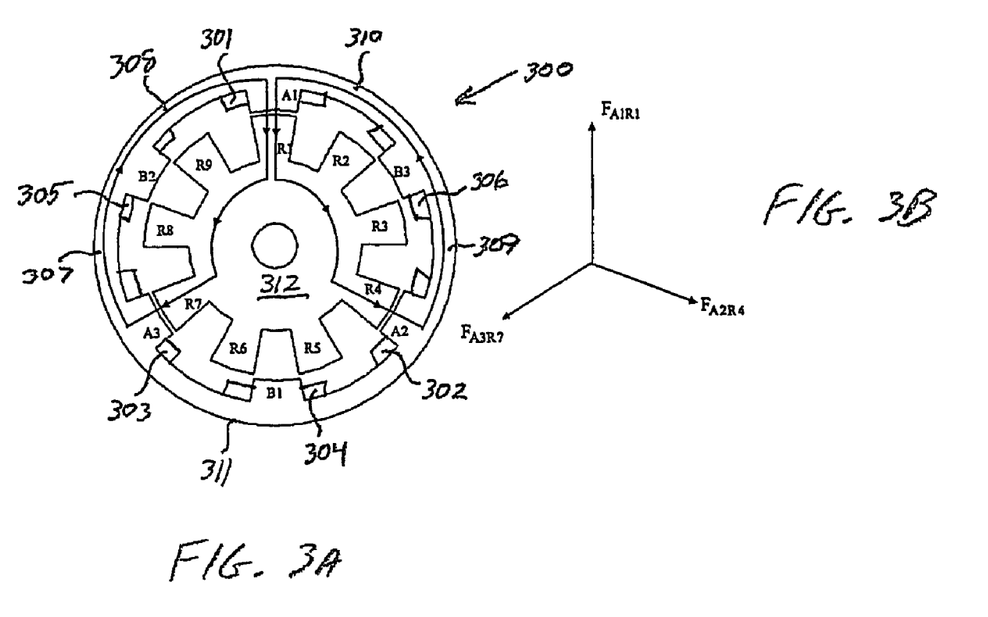
FIG. 3A illustrates a 6/9 TPSRM having its phase A poles excited when these poles are aligned with poles of the TPSRM's rotor.
FIG. 3B illustrates the normal forces produced at each of the phase A stator poles, of FIG. 3A, when phase A is excited.
Figure 4A:
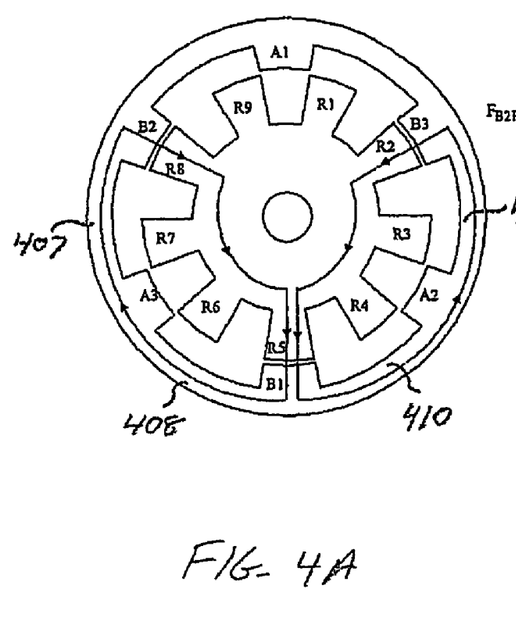
FIG. 4A illustrates the 6/9 TPSRM of FIG. 3 when the TPSRM's phase B poles are excited and aligned with poles of the TPSRM's rotor.

FIG. 3A illustrates a 6/9 TPSRM having its phase A poles excited when these poles are aligned with poles of the TPSRM's rotor. FIG. 4A illustrates the 6/9 TPSRM of FIG. 3 when the TPSRM's phase B poles are excited and aligned with poles of the rotor. The stator poles excited during phase A are stator poles A1, A2 and A3, and the stator poles excited during phase B are stator poles B1, B2 and B3. Stator poles A1-A3 and B1-B3 are excited by coils 301-303 and 304-306, respectively, wound around the poles. In an exemplary embodiment, the coils on each stator pole have an equal number of turns but may carry differing currents, though other configurations are possible. For the exemplary embodiment, the current in stator poles A1 and B1 is assumed to be I amperes. Coils 302, 303 on stator poles A2 and A3 are connected in parallel, so that the current coming into coil 301 of stator pole A1 is divided into equal parts for coils 302, 303 and has a value of I/2. Similarly, for coil 304 on stator pole B1, a current of I amperes passes through stator pole B1 and is divided equally into parallel coils 305, 306, wound on stator poles B2 and B3, so that they pass a current of I/2. With this configuration, the magneto motive force (mmf) provided by the currents flowing through coils 301, 304 of stator poles A1 and B1, respectively, is NI and is NI/2 for each of stator poles A2, A3, B2, and B3. The direction of the currents entering coils 301-306 of stator poles A1-A3 and B1-B3, as indicated by flux paths 307-310 and 407-410 respectively, implies a positive value mmf being exerted by each of stator poles A1 and B1 and a negative value mmf being exerted by each of stator poles A2, A3, B2, and B3.

Figure 4B:
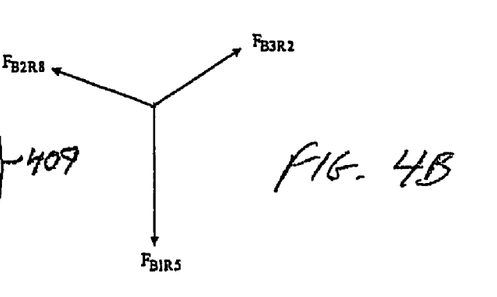
FIG. 4B illustrates the normal forces produced at each of the phase B stator poles of FIG. 4A when phase B is excited.

FIG. 3B illustrates the normal forces produced at each of the phase A stator poles of FIG. 3A, when phase A is excited. FIG. 4B illustrates the normal forces produced at each of the phase B stator poles of FIG. 4A, when phase B is excited. As illustrated by FIGS. 3B and 4B, the normal (i.e., radial) forces $F_{A1R1}$, $F_{A2R4}$, and $F_{A3R7}$ for stator poles A1-A3 combine to produce a vector sum of zero when phase A is excited and, similarly, normal forces $F_{B1R5}$, $F_{B2R8}$, and $F_{B3R2}$ for stator poles B1-B3 combine to produce a vector sum of zero when phase B is excited. Therefore, the resultant normal force exerted on the rotor by the stator is zero for all periods of operation. Moreover, since the individual radial forces pull in three different directions for each of phases A and B, they act to prevent the ovalization of the stator and, hence, mitigate stator acceleration induced by the transitions between the excitation of phases A and B. As a result, the invention reduces acoustic noise in TPSRM 300.

In the related art TPSRM 100 illustrated by FIGS. 1 and 2, the generated normal forces for each of the phase A and B excitations have the same magnitude and opposite directions (i.e., a 180 degree directional separation). These equal and oppositely directed forces induce an ovalization of the stator, as the resultant normal force is cancelled through the stator and rotor bodies. Moreover, since the phase A and B excitations induce ovalizations at right angles to one another, the stator is accelerated between phase excitations and, thereby, produces acoustic noise.

Another advantage of the invention results from the characteristic flux flow it produces in the back iron 311 of the stator, in particular. Referring to FIG. 3A, four flux paths exist in stator back iron 311. These four paths are flux path 307 between stator poles A3 and B2, flux path 308 between stator poles B2 and A1, flux path 309 between stator poles A2 and B3, and flux path 310 between stator poles B3 and A1. Four flux paths are also shown in FIG. 4A. These flux paths are flux path 407 between stator poles A3 and B2, flux path 408 between stator poles A3 and B1, flux path 409 between stator poles A2 and B3, and flux path 410 between stator poles B1 and A2. Of these eight flux paths, only flux paths 307, 309 and flux paths 407 and 409, respectively, overlap in the stator's back iron. Flux paths 307, 309 correspond to the excitation of phase A and flux paths 407, 409 correspond to the excitation of phase B. As may be seen by inspection of FIGS. 3A and 4A, flux paths 307 and 407 have the same direction of travel through the portions of stator back iron 311 through which both paths flow. Similarly, flux paths 309 and 409 have the same direction of travel through the portions of stator back iron 311 through which these flux paths flow. Therefore, no portion of stator back iron 311 experiences flux reversal during the operation of TPSRM 300. The absence of flux reversal in stator back iron 311 reduces core losses.

Still another advantage of the invention is that the flux reversal in segments of rotor back iron 312 occurs only once per revolution, which also reduces core losses. Stator poles A1-A3 and B1-B3 also do not experience any flux reversal, though rotor poles R1-R9 do.

Figure 5:
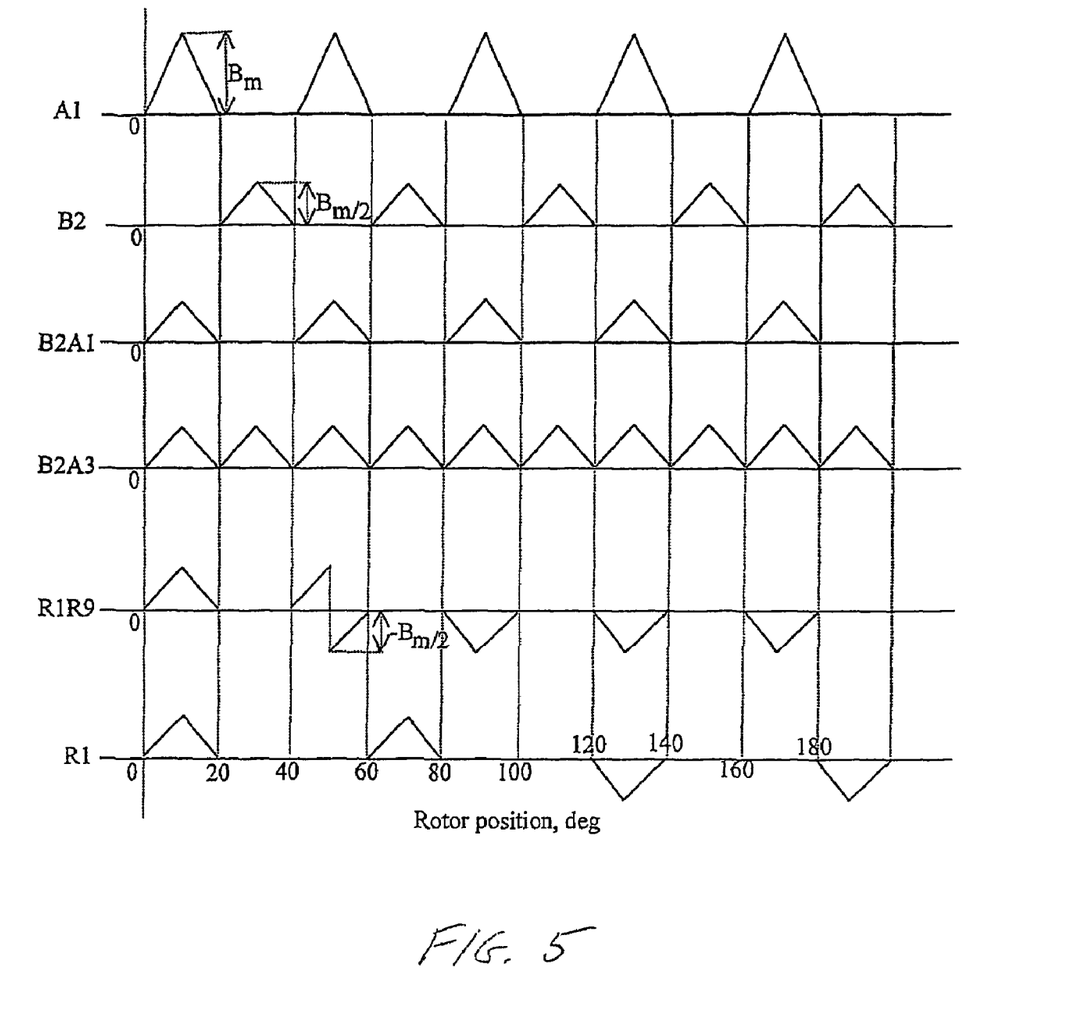
FIG. 5 illustrates representative waveforms of the flux density flowing through elements of the TPSRM illustrated in FIGS. 3A and 4A.

FIG. 5 illustrates representative waveforms of the flux density flowing through elements of TPSRM 300, illustrated in FIGS. 3A and 4A. In FIG. 5, the flux density waveforms for stator poles A1 and B2 are indicated by A1 and B2, respectively, and the flux density waveform for rotor pole R1 is identified by R1. The nomenclature R1R9 refers to the rotor back iron region between rotor poles R1 and R9. Similarly, the nomenclature B2A1 and B2A3 refer to the region between stator poles B2 and A1 and the region between stator poles B2 and A3, respectively. As may be determined by inspection of FIG. 5, a flux density reversal occurs in rotor back iron 312 once per revolution, but no flux density reversal occurs in stator back iron 311.

In FIG. 5, the magnitude value $B_m$ indicates the maximum flux density experienced by stator poles A1 and B1. Only stator poles A1 and B1 carry the maximum flux density value $B_m$. All other stator poles A2, A3, B2, and B3 carry a maximum flux density of $B_m/2$. As a result, all stator poles other than A1 and B1 can be half the size of stator poles A1 and B1, as each carries only half the flux of these poles. A considerable cost saving and weight reduction can be achieved with this arrangement. This may matter in aerospace applications where weight and volume minimization are critical factors in the selection of an electric machine.

The present invention eliminates flux reversals in the stator back iron and reduces or minimizes flux reversals in the rotor back iron. The stator back iron is defined for this invention as being all iron or ferromagnetic components in the stator, except the stator pole components, that convey the flux flowing through the rotor and stator. Because there are no flux reversals in the stator back iron, the hysteresis and eddy current losses in the iron decrease significantly, thus enhancing the efficiency of the machine.

In the rotor back iron (i.e., the back iron between adjacent rotor poles), the flux reversal occurs only once per rotor revolution, which is much less than occurs in conventional machines. For example, in a conventional 6/4 SRM, flux reversal in the rotor back iron may occur six times per rotor revolution, as described in Chapter 3 of Switched Reluctance Motor Drives, by R. Krishnan, CRC Press, 2001, which is hereby incorporated in its entirety into this specification. Four flux reversals occur in one revolution of the rotor in a conventional three-phase 12/8 machine.

Figure 6:
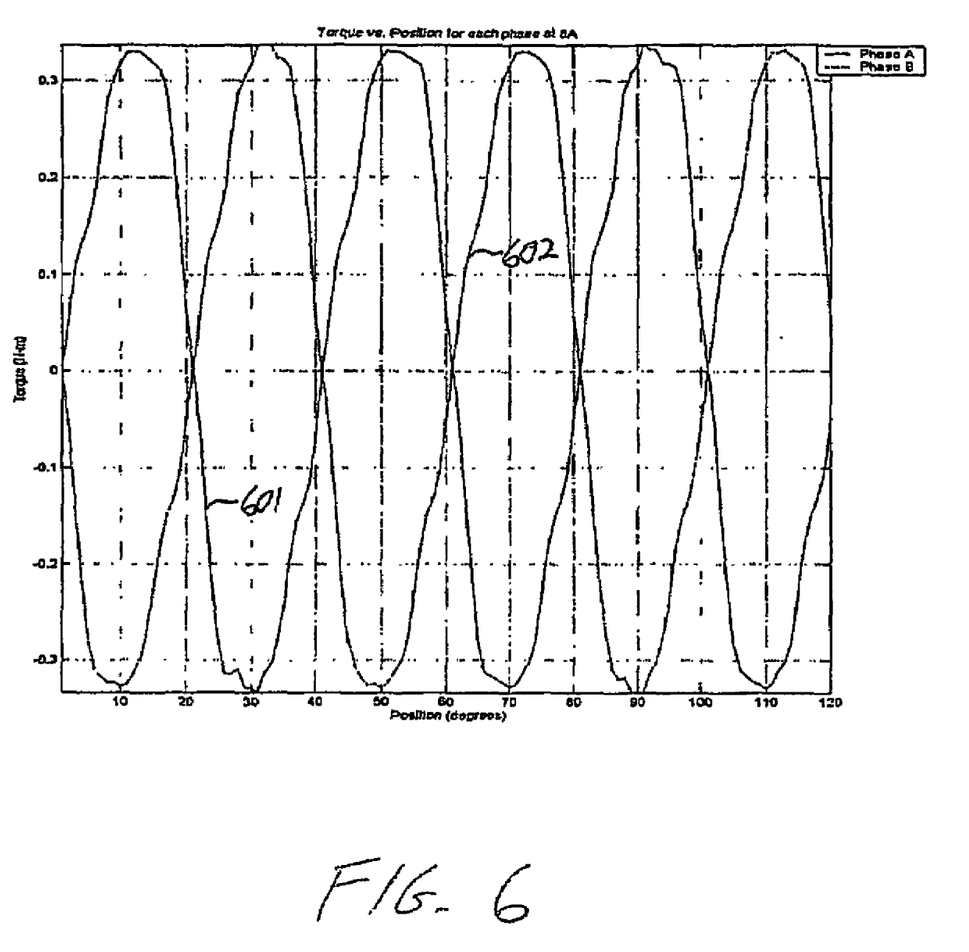
FIG. 6 illustrates a representative torque versus rotor position characteristic for the TPSRM illustrated by FIGS. 3A and 3B.

FIG. 6 illustrates a representative torque versus rotor position characteristic for the TPSRM illustrated by FIGS. 3A and 3B. As may be seen by inspection of FIG. 6, there are rotor positions for which the torque 601, 602 produced by each of phases A and B is zero. To produce a non-zero torque at all rotor positions, the rotor poles can be slotted, contoured, air-gap stepped, etc.

Figure 7:
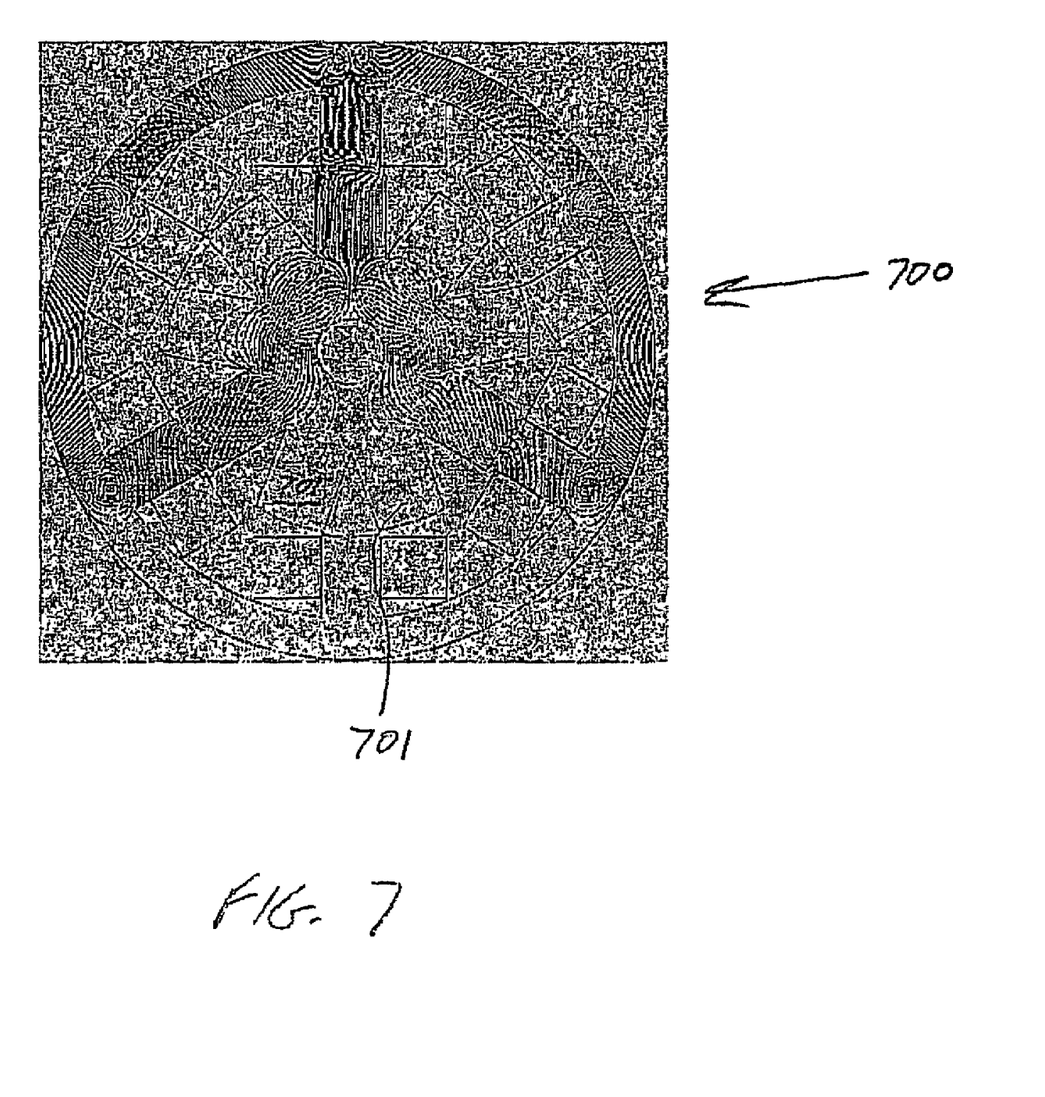
FIG. 7 illustrates a TPSRM having contoured rotor poles in which the radial length of each rotor pole decreases as the distal end curvature is traversed from one side to the other.
Figure 8:
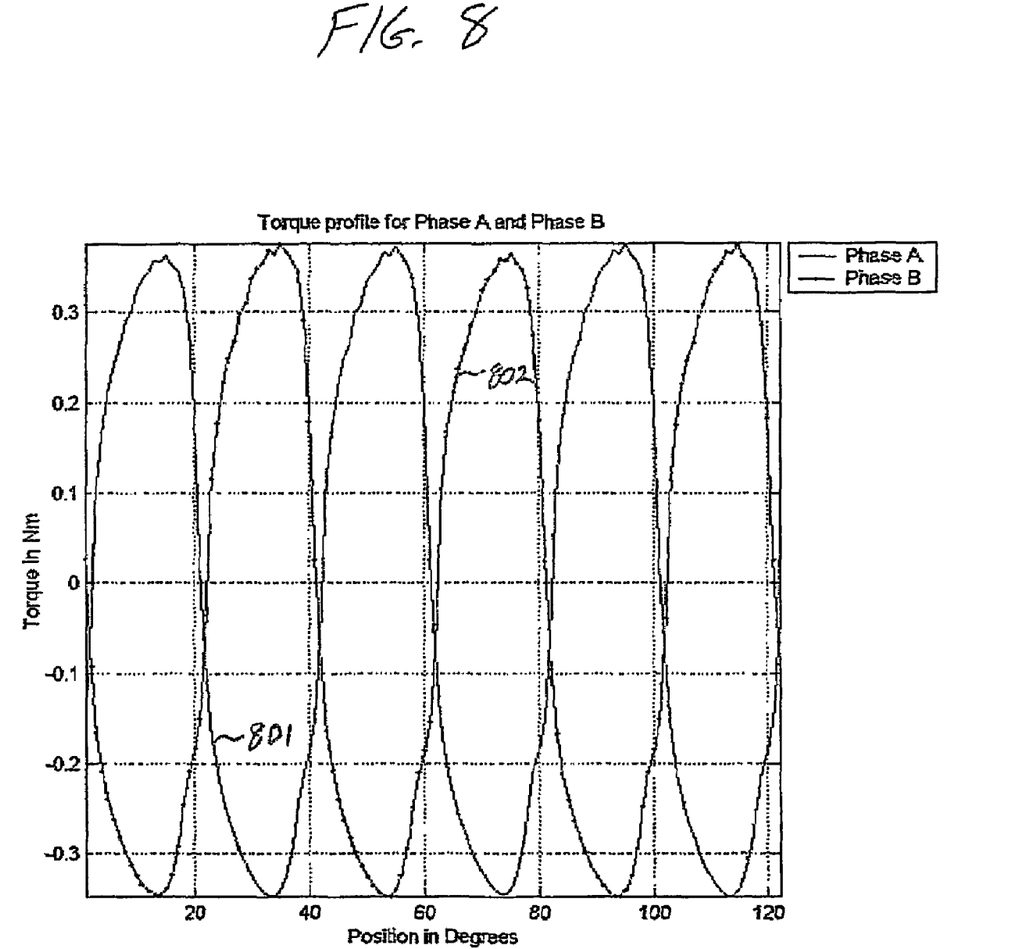
FIG. 8 illustrates a torque versus rotor position graph for the TPSRM of FIG. 7.

FIG. 7 illustrates a TPSRM having contoured rotor poles in which the radial length of each rotor pole decreases as the distal end curvature is traversed from one side to the other. FIG. 8 illustrates a torque versus rotor position graph for the TPSRM of FIG. 7. The torque for phase A is identified by reference character 801 and that for phase B is identified by reference character 802. The contouring of rotor pole 701 provides a non-uniform air gap across the pole face. As a result, the combined torque generated by TPSRM 700 has a non-zero value, considering both phases of the machine, at all times. This feature is crucial for supporting a self-starting capability for TPSRM 700 in both rotational directions of the shaft.

The present invention provides a force distribution similar to that of three phase ac machines, by distributing a stator current distribution among three windings. The three windings may constitute one phase of the SRM, as illustrated in FIGS. 3A and 4A. Alternatively, the SRM may have multiples of three windings in a phase with other combinations of total stator and rotor poles. The rationale for such a force distribution is that the normal forces are cancelled and uniformly distributed about the circle of rotation. Furthermore, the tangential forces can be distributed over two thirds of the periphery as opposed to only half the periphery, such as occurs where only two diametrically opposite poles contribute to the entire tangential force.

Figure 9A:
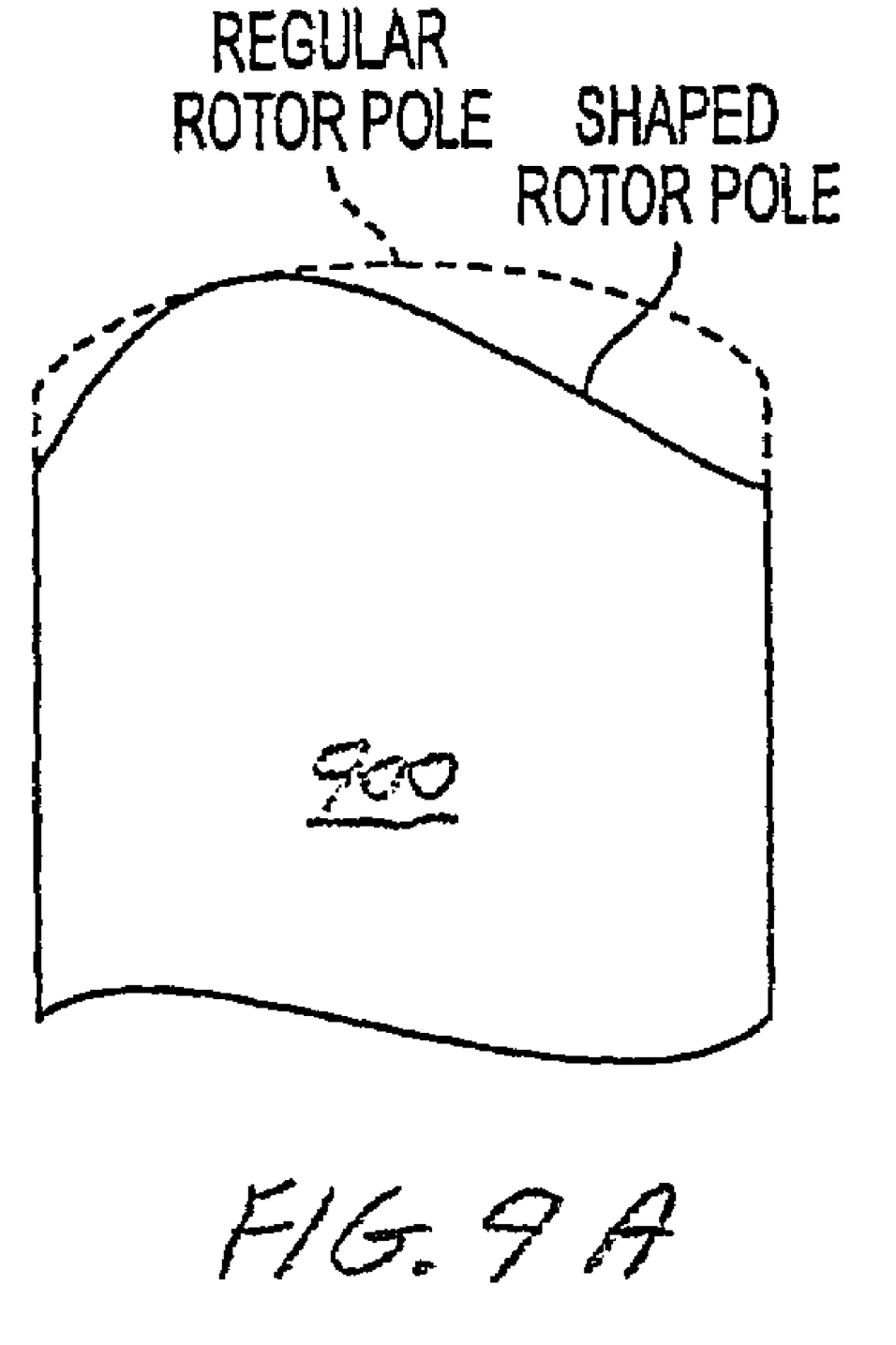
FIG. 9A illustrates a rotor or stator pole whose distal end face is shaped to induce a non-uniform flux density flow through the pole.
Figure 9B:
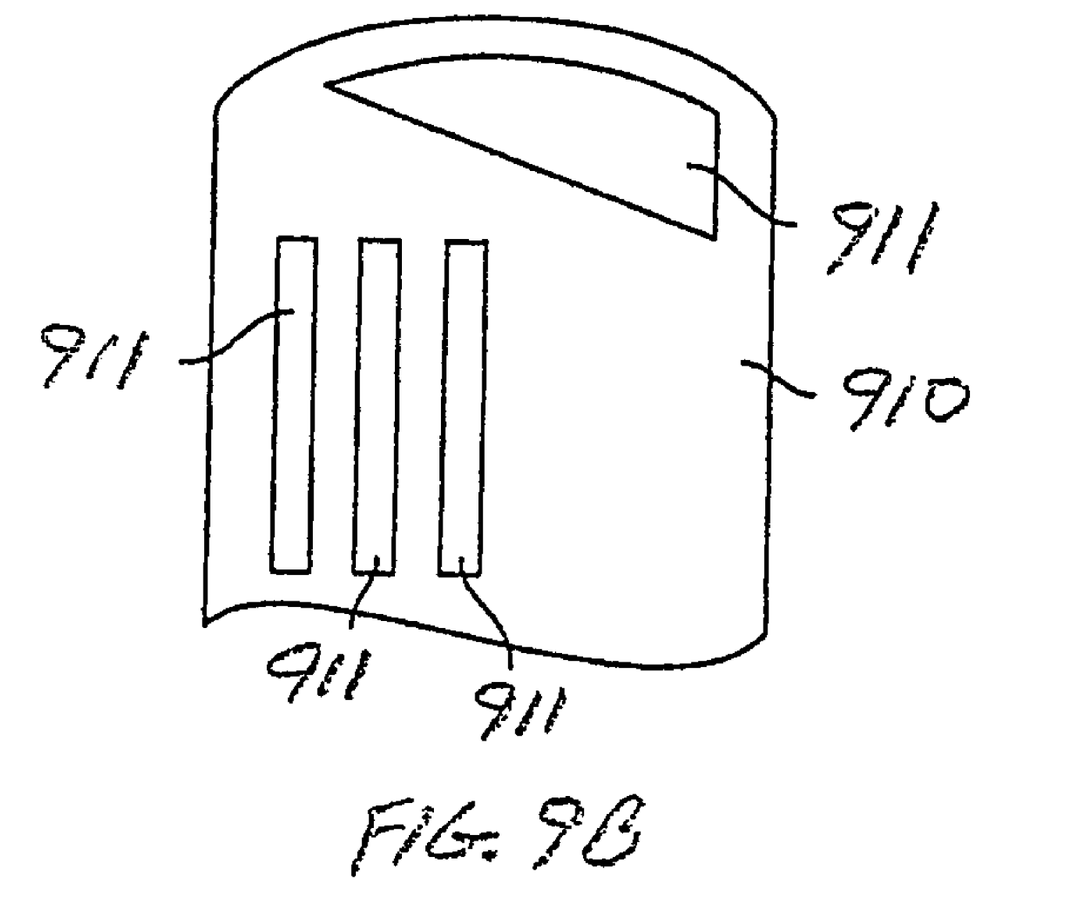
FIG. 9B illustrates a rotor pole that is slotted to induce a non-uniform flux density flow through the rotor pole.

FIG. 9A illustrates a rotor or stator pole whose distal end face is shaped to induce a non-uniform flux density flow through the pole. FIG. 9B illustrates a rotor pole that is slotted to induce a non-uniform flux density flow through the rotor pole. In FIG. 9A, rotor or stator pole 900 is shaped so that its distal end face has a non-uniform radius from the rotational axis of the rotor. In FIG. 9B, slots 911 are formed in rotor pole 910. With stator pole shaping or rotor pole shaping or slotting, or some combination thereof, the present invention can operate in both the clockwise and counter-clockwise directions with full four-quadrant capability, thereby providing a bidirectional start and run capability using only two phases.

The embodiment of the invention illustrated in FIGS. 3A and 4A is only one of many embodiments of the invention. Other embodiments may have different combinations of stator and rotor poles, such as the combinations of 6/3, 6/15, etc. The invention completely eliminates flux reversals in the stator back iron and reduces or minimizes the flux reversals in the rotor back iron to one reversal for each rotor revolution.

There are many advantages to having zero flux reversals in the stator back iron. These include: (1) reduced core losses and, hence, higher operating efficiency of the machine, (2) reduced vibration in the stator back iron and, hence, lower acoustic noise generated in the machine, and (3) a lower amount of required excitation, since there is no flux reversal in the machine, and hence higher operating efficiency.

Similarly there are advantages to having only one flux reversal per revolution in the rotor back iron of the machine. These advantages include reduced core losses, reduced excitation requirements, and reduced vibration induced by the rotor.

The present invention includes the unique pole combination of 6/9 for the stator and rotor with concentric windings for a two phase switched reluctance machine and its derivatives using the same principle of no flux reversals in the stator back iron. The stator poles may have differing numbers of winding turns around each pole of one phase of the machine, so as to distribute the normal and tangential forces as desired. Also, the winding currents on each pole can be controlled independently of other winding currents, thereby individually controlling the normal force around the periphery of the machine to produce a frictionless SRM. Furthermore, the TPSRM may be operated with the power converter topologies, described in Applicant's co-pending applications, that use either one controllable switch or two controllable switches for the control of currents and voltages in the windings of the machine for the two phases of the machine.

The foregoing description illustrates and describes the present invention. However, the disclosure shows and describes only the preferred embodiments of the invention, but it is to be understood that the invention is capable of use in various other combinations, modifications, and environments. Also, the invention is capable of change or modification, within the scope of the inventive concept, as expressed herein, that is commensurate with the above teachings and the skill or knowledge of one skilled in the relevant art.

The embodiments described herein are further intended to explain best modes known of practicing the invention and to enable others skilled in the art to utilize the invention in these and other embodiments, with the various modifications that may be required by the particular applications or uses of the invention. Accordingly, the description is not intended to limit the invention to the form disclosed herein.

What is claimed is:

1. A two-phase switched reluctance machine (TPSRM), comprising:
   a stator having a plurality of poles and a ferromagnetic or iron back material; and
   a rotor having a plurality of poles and a ferromagnetic or iron back material, wherein:
   current flowing through coils wound around a first set of the plurality of stator poles induces a flux flow through the first set of stator poles and portions of the stator back material during a first excitation phase, said coils wound around said first set of the plurality of stator poles having an equal number of turns but carrying differing currents, current flowing through coils wound around a second set of the plurality of stator poles induces a flux flow through the second set of stator poles and portions of the stator back material during a second excitation phase, and the numbers of stator and rotor poles are selected such that substantially no flux reversal occurs in any part of the stator back material as a result of transitioning between the first and second excitation phases.

2. The TPSRM of claim 1, wherein the number of stator poles is 6 and the number of rotor poles is 3.

3. The TPSRM of claim 1, wherein the number of stator poles is 6 and the number of rotor poles is 9.

4. The TPSRM of claim 1, wherein the number of stator poles is 6 and the number of rotor poles is 15.

5. The TPSRM of claim 1, wherein the stator or rotor poles provide a non-zero combined torque for all rotational positions of the rotor during which at least one of the first and second phases is excited or a transition is occurring between the first and second phase excitations.

6. The TPSRM of claim 5, wherein the distal end faces of the stator or rotor poles are contoured to have a non-uniform radius from the rotor's axis of rotation.

7. The TPSRM of claim 5, wherein the rotor poles are slotted.

8. The TPSRM of claim 1, wherein one stator pole in each of the first and second sets has a maximum flux density flow rate that is about twice the maximum flux density flow rate of the other stator poles in the set.

9. The TPSRM of claim 1, wherein one stator pole in each of the first and second sets conveys about twice or more the amount of flux density conveyed by the other stator poles in the set.

10. The TPSRM of claim 1, wherein the coil wound around one stator pole in each of the first and second sets has twice the number of windings as the coils wound around the other stator poles in the set.

11. The TPSRM of claim 1, wherein further comprising a controller that provides about twice as much current to the coil wound around one stator pole in each of the first and second sets as is provided to the other stator poles in the set.

12. The TPSRM of claim 1, wherein the numbers of stator and rotor poles are further selected such that a flux reversal occurs only once in any part of the rotor back material, excluding the rotor poles, per revolution of the rotor as a result of transitioning between the first and second excitation phases.

13. The TPSRM of claim 1, wherein the vector sum of normal forces exerted by the stator poles, in response to the first and second excitation phases, at any instant of time is EGICO.

14. A two-phase switched reluctance machine (TPSRM), comprising:

a stator having a plurality of poles and a ferromagnetic or iron back material; and a rotor having a plurality of poles and a ferromagnetic or iron hack material, wherein:

current flowing through coils wound around a first set of the plurality of stator poles induces a flux flow through the first set of stator poles and portions of the stator back material during a first excitation phase, said coils wound around said first set of the plurality of stator poles having an equal number of turns but carrying differing currents, current flowing through coils wound around a second set of the plurality of stator poles induces a flux flow through the second set of stator poles and portions of the stator back material during a second excitation phase, and the numbers of stator and rotor poles are selected such that a flux induced by each of the first and second excitation phases flows through a path encompassing about two-thirds of the circumference of each of the rotor and stator back materials.

15. A method of operating a two-phase switched reluctance machine (TPSRM), comprising:

providing coils around a first set of a plurality of stator poles of the TPSRM, said coils having an equal number of turns;

inducing an electromagnetic flux to flow through the first set of poles of the stator of the TPSRM during a first excitation phase, wherein differing currents are caused to flow through said coils;

inducing an electromagnetic flux to flow through a second set of poles of the stator during a second excitation phase; and transitioning between the first and second excitation phases without creating a substantial flux reversal in a ferromagnetic or iron back material of the stator.

16. The method of claim 15, wherein the electromagnetic flux induces a torque to a rotor of the TPSRM and the combined torque provided by both the first and second excitation phases produces a non-zero value for all rotational positions of the rotor during which at least one of the first and second phases is excited or a transition is occurring between the first and second phase excitations.

17. The method of claim 15, wherein one stator pole in each of the first and second sets has a maximum flux density flow rate that is about twice the maximum flux density flow rate of the other stator poles in the set.

18. The method of claim 15, further comprising inducing about twice as much flux density to flow in one stator pole in each of the first and second sets as flows in the other stator poles in the set.

19. The method of claim 15, wherein a flux reversal substantially occurs only once in any part of a ferromagnetic or iron back material of a rotor of the TPSRM, excluding poles of the rotor, per revolution of the rotor as a result of transitioning between the first and second excitation phases.

20. The method of claim 15, further comprising regulating the electromagnetic flux flow through the stator poles during each of the first and second excitation phases to exert substantially a zero value vector sum of normal forces by the stator poles at any instant of time during the first or second excitation phases.

* * * * *

UNITED STATES PATENT AND TRADEMARK OFFICE
CERTIFICATE OF CORRECTION

PATENT NO. : 7,579,734 B2  Page 1 of 1
APPLICATION NO. : 10/549800
DATED : August 25, 2009
INVENTOR(S) : Ramu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 538 days.

Signed and Sealed this

Fourteenth Day of September, 2010

David J. Kappos
*Director of the United States Patent and Trademark Office*